(12) United States Patent
Russo et al.

(10) Patent No.: US 6,335,408 B1
(45) Date of Patent: Jan. 1, 2002

(54) COPOLYMERS OF PERFLUORODIOXOLES

(75) Inventors: Antonio Russo; Walter Navarrini, both of Milan (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/249,853

(22) Filed: Feb. 16, 1999

(30) Foreign Application Priority Data

Feb. 17, 1998 (IT) .......................................... MI98A0291

(51) Int. Cl.[7] .................................................. C08F 14/18
(52) U.S. Cl. ........................ 526/253; 526/209; 526/242; 526/255
(58) Field of Search ................. 526/242, 255, 526/209, 247

(56) References Cited

U.S. PATENT DOCUMENTS

| | | | |
|---|---|---|---|
| 3,642,742 A | | 2/1972 | Carlson |
| 3,865,845 A | | 2/1975 | Resnick |
| 5,051,114 A | * | 9/1991 | Nemser et al. ................. 55/16 |
| 5,194,482 A | * | 3/1993 | Logothesis et al. .......... 524/494 |
| 5,235,074 A | | 8/1993 | Navarrini et al. |
| 5,260,492 A | * | 11/1993 | Feiring et al. ............... 568/685 |
| 5,710,345 A | * | 1/1998 | Navarrini et al. ........... 568/596 |
| 5,916,971 A | * | 6/1999 | Koike et al. ................. 525/197 |

FOREIGN PATENT DOCUMENTS

| | | |
|---|---|---|
| EP | 0 076 581 A | 4/1983 |
| EP | 0 076 581 | 4/1983 |
| EP | 0 080 187 | 6/1983 |
| EP | 0 184 459 | 6/1986 |
| EP | 0 633 257 | 1/1995 |
| GB | 2 211 845 A | 7/1989 |
| GB | 2211845 | 12/1989 |
| WO | WO 91/03472 | 3/1991 |

OTHER PUBLICATIONS

"Structure–Property Relationship of Fluorinated Dioxole Polymers", Ming Hung, Macromolecules, 1993, 26, pp. 5829–5834.

"Thermal Rearrangement of Fluorinated Dixoles", Ming Hung et al., J. Am. Chem. Soc., 1990, 112, pp. 9671–9672.

"Redox Polymerization", Prog. Polym. Sc. vol. 8, pp. 61–131, 1982.

"Novel Elimination Reactions of Telomer Iodides of 1,1–Difluoroethylene", Murray Hauptschein et al., J. Am. Chem., Soc., vol. 82, 1960, pp. 2868–2871.

"Bis (fluoroxy) difluoromethane, $CF_2(OF)_2$"; F. A. Hohorst et al., J. Am. Chem. Soc. vol. 87, Apr. 12, 1967, pp. 1809–1810.

"Bis (perfluoralkyl) Trioxides[1]" Phillip G. Thompson, J. Am. Chem. Soc. Aug. 16, 1967, vol. 89; pp. 4316–4319.

"Fluorocarbonyl Hypofluorite", Cauble et al.; J. Am. Chem. Soc. vol. 87, 1967, pp. 5161–5162.

"Free Radical Additions Involving Fluorine Compounds. IV. The Addition of Dibromodifluoromethane to Some Fluoroolefins[1]"; Tarrant et al., J. Am. Chem. Soc. vol. 77, 1955 pp. 2783–2787.

* cited by examiner

*Primary Examiner*—David W. Wu
*Assistant Examiner*—Tanya Zalukaeva
(74) *Attorney, Agent, or Firm*—Arent Fox Plotkin Kintner Kahn PLLC.

(57) ABSTRACT

Copolymers of perfluoro-4-alkyl-1,3-dioxoles having the general formula (I)

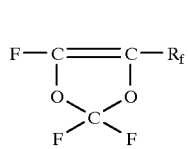

wherein $R_f$ is a perfluoroalkylic radical having from 1 to 5 carbon atoms, allow to prepare copolymers with Tg higher than those of the copolymers containing the same molar percentage of fluorinated dioxoles of the art.

4 Claims, No Drawings

COPOLYMERS OF PERFLUORODIOXOLES

The present invention relates to a class of dioxoles, and more specifically it relates to TFE copolymers with dioxoles, said copolymers having a higher Tg in the range 0.1–50% by moles of dioxole, in comparison with the copolymers of TFE with the known dioxoles.

Various structures of dioxoles have been described in the art. The U.S. Pat. No. 3,865,845 describes the perfluorodimethyldioxole (PDD) having the formula:

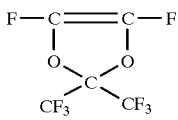

The patent EP 76,581 describes the following class of halo-perfluoroalkyl-dioxoles:

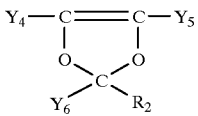

wherein $Y_4$, $Y_5$ and $Y_6$ are F or Cl, while $R_2$ is a perfluoroalkyl radical having from 1 to 4 carbon atoms.

The patent EP 80,187 relates to 2,2,4,5-tetrafluoro-1,3-dioxole (PD) having the formula:

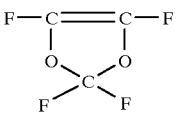

The patent EP. 633,257 relates to the following class of perfluoroalkyl-perfluoroalkoxy dioxoles having the formula:

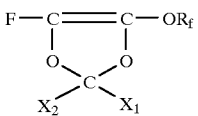

wherein $R_f$ is a perfluoroalkyl radical having from 1 to 5 carbon atoms; $X_1$ and $X_2$ are, independently from each other, F or $CF_3$.

The drawback of the perfluorodioxoles described in the U.S. Pat. 3,865,845, EP 80,187 and EP 76,581 is that they tend to spontaneously homopolimerize.

For example the perfluorodioxole (PD) of EP 80,187 tends to homopolymerize also at very low temperatures such as −78° C. Therefore this substance is not stable. A further drawback is that in the copolymerization products it is difficult to have an homogeneous distribution of the components along the chain.

In the GB patent 2,211,845 a process is described to obtain dioxoles having formula:

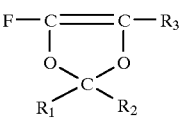

wherein $R_1$ and $R_2$ are independently selected from fluorine, chloroalkyl and $C_1$–$C_3$ fluoroalkyl; $R_3$ is fluorine, or chlorine, or $C_1$–$C_3$ perfluoroalkyl. In this patent reference is made to the U.S. Pat. 3,865,845 (see above) for the obtainment of dioxolanes from which the dioxoles having the above mentioned formula are obtained. This patent (GB 2,211,845) does not give any indication about the properties of the obtainable copolymers and in particular about the Tg.

In the art, the reactivity of substituted perfluoroalkyl dioxoles that is of perfluoro-2,2,4-trimethyl-1,3,-dioxole (PTD) (Ming-H. Hung, Macromolecules 26, 5829-5834, 1993) having the formula

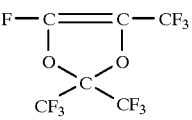

has been studied.

This compound is obtained by reacting hexafluoroacetone with 2,3 epoxy-1-propanol (M. H. Hung, J. Can. Chem. Soc. 1990, 112, 9672).

The PTD dioxole shows a poor reactivity: it lowers the polymerization kinetics, it does not homopolymerize and is not capable to copolymerize with TFE. The PTD low reactivity can be attributed to the steric effects of the 4 position trifluoromethyl group.

As regards the processes to obtain (per)fluorodioxoles, according to the art, the preparation of these compounds is carried out from the corresponding dioxolanes having a chlorine atom respectively in the 4 and 5 positions by dehalogenation reaction with metals such as Mg, Zn, in particular Mg. These reactions are carried out in organic solvent such as dioxane, DMF, in particular dimethylformamide (see U.S. Pat. No. 3,865,845, EP 76,581, EP 80,187). Reactions using polluting solvents are involved, whose disposal is difficult. In the art (WO 91/03472) it has moreover been shown that the dehalogenation yield increases when the dioxolane the anti isomer amount (the isomery is referred to the position of the two chlorine atoms in the molecule) is higher than that of the sin isomer.

The need was felt to obtain perfluorodioxoles allowing to prepare copolymers with olefinic comonomers, in particular TFE, having a Tg higher than the copolymers of the art with the same dioxole content.

A higher Tg value allows the use of the polymers at higher temperature.

It has been now surprisingly and unexpectedly found that it is possible to overcome this problem by means of a novel class of perfluorodioxoles, which are obtained with high yields by a new process more favourable to the environment than the known one.

An object of the present invention is a class of perfluoro-4-alkyl-1,3-dioxoles having the general formula:

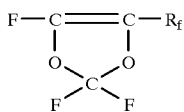
(I)

wherein $R_f$ is a perfluoroalkylic radical having from 1 to 5 carbon atoms.

Surprisingly said class of dioxoles copolimerizes with olefinic monomers even if the perfluoroalkyl substituent is present in the 4 position of the ring, to the steric effects of which the PTD low reactivity has been attributed, as seen in the art.

In examining the prior art, it has been noticed that factors of steric type, due to the presence of groups directly bound to the carbon atoms in position 4 or 5 of the dioxolene ring, are capable to lessen or hinder the polymerization processes.

Surprisingly, the compounds of formula (I) are, on the contrary, capable to easily (co)polymerize.

The preferred compound in the general formula is perfluoro-4-methyl-1,3-dioxole (PMD) having the formula (II):

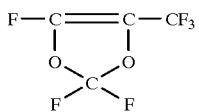
(II)

A further object of the present invention are the copolymers with monomers containing olefinic or of olefinic type unsaturations, obtainable with the compounds of formula (I), containing from 0.1 to 50% by moles of the following unit:

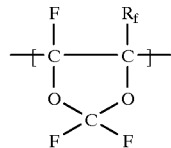
(III)

wherein $R_f$ is a perfluoroalkylic radical as above defined.

These polymers show a more homogeneous composition along the chain, also when the dioxoles concentration in the polymer is higher than 12% by moles.

The perfluorodioxoles of the invention can copolymerize with one or more comonomers having oelfinic unsaturations, such as for example, differently from PTD, tetrafluoroethylene.

It is surprising and unexpected that the copolymers with TFE in which the dioxole content of the invention is in the range 0.1–50% by moles have an improved Tg in comparison with the TFE copolymerized with the known dioxoles.

The monomers of the invention can copolymerize with vinyilidene fluoride, vinyl fluoride, trifluoroethylene, perfluoropropene, perfluoromethylvinylether, perfluoroethylvinylether, perfluorodioxole PD, perfluoro (2,2-dimethyl)-1,3-dioxole, perfluoro-4-methoxy-1,3-dioxole, $CF_2=CF—O—CF_2—CF_2—SO_2F$, $CF_2=CF—(OCF_2(CF_3) CF)_n—O—CF_2—CF_2—SO_2F$ wherein n is an integer from 1 to 3, chlorotrifluoroethylene, vinyl chloride, methyl (meth)acrylate, butyl (meth)acrylate, ethylene.

The copolymers can be prepared by polymerization of radical type, both in aqueous and organic medium.

In the aqueous medium polymerizations, the polymerization initiator can be any substance capable to produce radicals, such as for instance peroxides, persulphates or azo-compounds. These compounds in the reaction conditions have an average life such as to allow to obtain the polymer with the desired molecular weight. Also a reducing agent can optionally be used, such as for instance an iron salt, in order to promote the initiator decomposition.

The used initiator amount depends, as known, on the polymerization temperature, on the optional transfer agent presence, on the desired molecular weight and generally on the employed reaction conditions. The aqueous medium polymerization requires the presence of an emusifying agent. See for instance EP 184,459.

Alternatively, the polymerizations can be carried out in organic solvent as described in U.S. Pat. No. 3,642,742. Any initiator suitable to the TFE polymerization in organic solvent can be used. Preferably the initiator must be soluble in the reaction solvent. Examples of initiators are alkylpercarbonates, perfluoroacylperoxides, benzoyl peroxide and azo-bis(isobutyronitrile).

Redox systems can also be used such as those described in Prog. Polym. Sci, 8, 61 (1982). The solvent is generally selected from (hydro) (chloro) fluorocarbons and (hydro) perfluoropolyethers, when H is present it is in one or both ends, preferably in both.

The novel polymers have Tg higher than those of the polymers of the art containing the same dioxole percentage, as shown in Table 1.

As already said, higher Tg values allow a greater flexibility of the polymer use at high temperatures.

The TFE crystalline copolymers are used to prepare dielectric materials.

Amorphous copolymers containing the invention dioxoles are used for coating of electric wires and of parts to be insulated, besides in the optical fibers field, due to their low refraction index.

The amorphous copolymers use higher amounts of comonomer in comparison with the crystalline copolymers. This depends on the various types of comonomer used. The skilled in the art can easily determine the invention dioxole amount for obtaining amorphous copolymers by determining with the known analytical methods of the art the disappearance of the crystalline domains. Generally in the crystalline copolymers the % by moles of dioxole is lower than 15% by moles.

A further object of the present invention is a process for preparing with high yields the perfluorodioxoles of the invention, characterized in that the dioxolanes containing in position 4 of the ring a fluorine atom and a second halogen selected from F, Cl and Br, and in position 5 an hydrogen atom, are submitted to dehydrohalogenation reaction in alkaline solution.

When in position 4 a Cl or Br atom is present, it has been found that the dehydrohalogenation reaction is selective towards the removal of HCl or HBr, respectively, also when the dioxolane molecule contains fluorine atoms in vicinal position with respect to the C-H group, and, therefore, HF elimination could take place.

Moreover it has been found that the yields of the new process are independent from the percentages of sin and anti isomers present in the starting dioxolane.

The dehydrohalogenation reaction is carried out in KOH or NaOH aqueous solutions in phase transfer conditions, for example in a KOH solution having a concentration in the range 20–60% by weight, preferably 30–50%; the reaction temperature is in the range 20°–100° C., preferably 300°–800° C. The phase transfer agent can be a phosphonium salt or a quaternary ammonium salt. In this way the problem solution of the reaction mother liquors disposal is made much easier with respect to the prior art.

The perfluoro dioxoles of the present invention can be prepared by reacting, in a first step (reaction a) an olefin of formula $R_f$—CH=CFX (X=F, Cl, Br), wherein $R_f$ is a radical as above defined, with hypofluorite gas $CF_2(OF)_2$ (BDM) and by subjecting in a second step (reaction b) the obtained dioxolanes to dehydrohalogenation in KOH or NaOH aqueous solutions according to the following process:

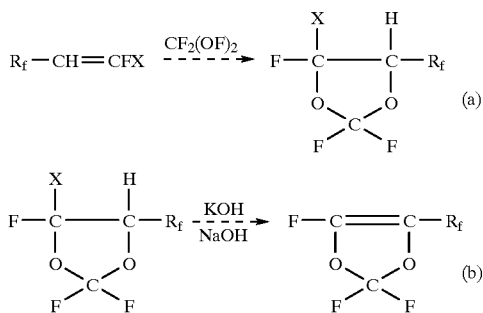

The reaction a) is carried out at temperatures in the range −140° C./+60° C., preferably −110° C./−20° C., and leads to the dioxolane obtainment.

The olefin of formula $R_f$-CH=CFX wherein X=F can be perpared according to the following general scheme (M. Murray et al. J. Am. Chem. Soc. 82, 2868 (1960):

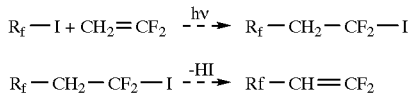

Instead of the fluorine atom on the carbon in position 1 also a chlorine or bromine atom can be introduced according to the methods known in the art.

The olefin is in liquid phase and preferably is mixed with a solvent selected from (hydro) (chloro)fluorocarbons and/or (hydro)perfluoropolyethers, when H is present it is in one or both terminal ends, preferably in both (ex. Galden®, H-Galdenv®, Fomblin®, Krytox® Demnum®). Among the latter, those having a molecular weight comprised between 500 and 1000 are preferred.

The hypofluorite or bis (fluoroxy) difluoromethane (BDM) is preferably fed in a continuous way, in gaseous phase and preferably diluted with an inert gas such as for example $N_2$, He or Ar. The ratio between the volume of the diluent gas and the hypofluorite is generally in the range 3–10, preferably 3–6.

The bis(fluoroxy)difluoromethane is a known compound and can be prepared for example as described in F.A. Hohorst, J.M. Shreeve, *J.Am.Chem.Soc.*87, 1809 (1967); P.J. Tompson, *J.Am. Chem.Soc.* 89, 4316 (1967); R.L. Cauble e G.H. Cady, *J.Am. Chem.Soc.* 87, 5161 (1967).

The dehydrohalogenation reaction b) is carried out as previously described.

The final compounds are distilled from the reaction crude material and, as said, can be indefinitely kept at room temperature.

A further object of the present invention is the synthesis of the dioxole of formula (II) (PMD) according to the following synthesis scheme:

a') radical addition of bromo-chloro-difluoromethane $CF_2BrCl$ to 1,1-difluoroethylene (VDF) $CH_2=CF_2$ to obtain the compound having the formula $BrCF_2$—$CH_2$—$CF_2Cl$;

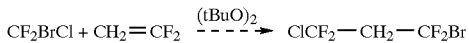

b') dehydrohalogenation reaction of the compound $BrCF_2$—$CH_2$—$CF_2Cl$ in phase transfer conditions in KOH aqueous solution, and formation of the olefin having the formula $ClCF_2$—CH=$CF_2$;

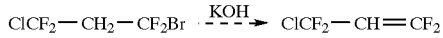

c') re-arrangement of the $ClCF_2$—CH=$CF_2$ olefin catalyzed by $AlCl_3$ and formation of the olefin of formula $CF_3$—CH=CFCl;

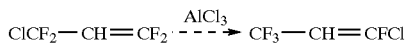

d') addition of bis(fluoroxy)difluoromethane to the $CF_3$—CH=CFCl olefin with formation of the dioxolane:

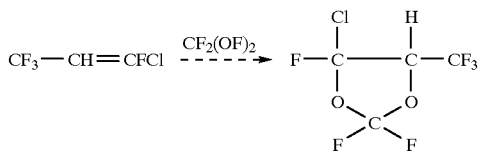

e') dioxole formation by dehydrohalogenation of the dioxolane in KOH or NaOH aqueous solutions:

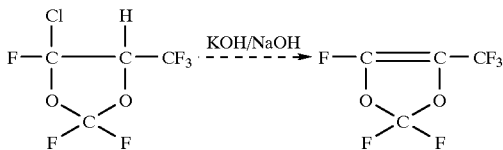

The reaction (a') occurs in the presence of initiators such as for example azo-compounds or peroxides; the reaction tmperature is selected in connection with the used initiator and generally is in the range 60°–130° C.; the molar ratio between $CF_2BrCl$ and VDF is in the range 2–10, preferably 3–6. The presence of solvents is not necessary.

For the use of $CF_2Br_2$ as a telogen, reference is made to the paper by P. Tarrant, A.M. Lovelace and M.R. Lilyquist, *J. Am.Chem.Soc.*77, 2783 (1955).

The reaction (b') is carried out in phase transfer conditions, in KOH aqueous solution having a concentration in the range 20–60% by weight, preferably 30–50%; the reaction temperature is in the range 20°–100° C., preferably 30°–70° C.; the phase transfer agent can indifferently be a phosphonium salt or a quaternary ammonium salt; the reaction is carried out at the reduced pressure of 600–100 mmHg, preferably 500–200 mmHg. The reduced pressure allows to remove from the reaction medium the $ClCF_2$—CH=$CF_2$ olefin which is obtained with high yields, and which is collected in a trap at low temperature directly connected with the reactor.

The reaction (c') is carried out with an amount by moles of $AlCl_3$, in the range 2–20%, preferably 5–15% with respect to the olefin moles ClCF$_2$-CH=CF$_2$; the reaction temperature is in the range −50°/+30° C., preferably −30/+20° C. In this step the presence of solvents is not necessary.

The reaction (d') and the subsequent one (e') are carried out as described for the obtainment of perfluorodioxoles.

The following examples are given for illustrative purposes and do not limit the scope of the present invention.

EXAMPLE 1

Preparation of 4-chloro-5-trifluoromethyl-2,2,4-trifluoro-1,3-dioxolane

Example 1a

Preparation of 1-bromo-3-chloro-1,1,3,3-tetrafluoropropane BrCF$_2$–CH$_2$–CF$_2$Cl In a 370 ml steel autoclave, equipped with mechanical stirrer and thermocouple, 280 g of CF$_2$BrCl (1.69 moles) and 2.8 g (0.019 moles) of di-terbutylperoxide, are introduced.

The so charged autoclave is brought, by an heating jacket, to 110° C. At this temperature, under mechanical stirring, VDF is fed up to a pressure inside the autoclave equal to 20 atm. The VDF pressure is maintained in the range 15–20 atm during the reaction (about 8 h). The addition of VDF is interrupted when the total amount of the added compound is of 65 g (1.01 moles)

From the reaction crude material, by fractionated distillation in a plate column, the reaction products are separated. The following fractions having boiling point ±1° C. with respect to the temperatures reported hereunder are collected:
−2° C.: 110 g (0.66 moles) of unreacted CF$_2$BrCl (MW 165.5)
+85° C.: 145 g (0.63 moles of BrCF$_2$—CH$_2$—CF$_2$Cl (MW 229.5).

In the distillation boiler 90 g of a oligomer mixture remains, having the general formula ClCF$_2$(CH$_2$CF$_2$)$_n$CH$_2$CF$_2$Br with n=1–4. The yield in addition product, defined as the ratio between the obtained moles of ClCF$_2$CH$_2$CF$_2$Br and the used VDF moles, is equal to 62%. Characterization of 1-bromo-3-chloro-1,1,3,3-tetrafluoropropane.

Boiling point: 85° C.
$^{19}$F-NMR in ppm referred to CFCl$_3$=0;
−46.6(2F, ClCF$_2$); −41.9 (2F, BrCF$_2$).
H-NMR in ppm referred to TMS=0:
+3.2(2H, —CH$_2$—)
Mass spectrum (EI), main bands and attributions:
195 (M−Cl+); 149 (M−Br+, 100%); 129 (BrCF$_2$+); 85 (ClCF$_2$+).
IR, main bands (cm$^{-1}$):
2980, 1364, 1218, 1182, 1148, 938, 800, 692, 642, 566.

Example 1b

Dehydrobromination of 1-bromo-3-chloro-1,1,3,3,-tetrafluoropropane.

In a 100 ml three-necked glass flask equipped with magnetic stirrer, thermometer, dropping funnel, reflux condenser, and cold trap (liq. N$_2$) directly connected to the reflux condenser, 25 g (0.11 moles) of ClCF$_2$CH$_2$CF$_2$Br and 1.5 g (0.005 moles) of tetrabutylanmonium hydroxide, are introduced. The reaction mixture is heated up to 45° C. by an oil bath; at this point, under vigorous stirring and a residual pressure of 400 mmHg, 25 ml of an aqueous solution of KOH at 30% by weight (equivalent to 11.83 or 0.2 moles of KOH) are dropped, maintaining the reaction mixture temperature in the range 45–50° C. When the addition is over, the residual pressure is brought to 200 rmHg and 14.9 g of material are collected in the cold trap.

By fractionated distillation in a plate column at atmospheric pressure of the reaction crude material, 13.7 g (0.092 moles) of the ClCF$_2$-CH=CF$_2$ olefin, are recovered.

The yield in dehydrobromination product calculated as the ratio between the obtained moles of ClCF$_2$CH=CF$_2$ and the starting moles of ClCF$_2$CH$_2$CF$_2$Br, is 83.6%.
Characterization of the 3-chloro-1,1,3,3-tetrafluoropropene
Boiling point=+14° C.
$^9$F-NMR in ppm referred to CFCl$_3$=0;
−51(2F, ClCF$_2$—); −71.6 (1F, =CF); −78.5(1F, =CF)
$^1$H-NMR in ppm referred to TMS=0:
+5(1H, —CH=).
Mass spectrum (EI), main bands and attributions:
148 (M+); 129 (M-F+); 113 (M-Cl+ 100%); 85 (ClCF$_2$+); 63 (C$_2$F$_2$H+)
IR, main bands (cm$^{-1}$):
3144, 3098, 1758, 1372, 1269, 1227, 1098, 1008, 935, 831, 792, 580.

Example 1c

Isomerization of the 3-chloro-1,1,3,3-tetrafluoropropene to 1-chloro-1,3,3,3-tetrafluoropropene.

In a 50 ml three-necked glass flask, equipped with magnetic stirrer, thermometer and cold trap (liq. N$_2$) directly connected with the flask by means of a retort, in inert gas atmosphere (N$_2$) and at the temperature of −30° C., 16.2 g (0.109 moles) of ClCF$_2$—CH=CF$_2$ are introduced. In these conditions 1 g (0.007 moles) of AlCl$_3$ is then added, under stirring. The temperature of the reaction mixture is slowly allowed to raise up to 13° C., then the system pressure is lowered to 400 mmHg. In the cold trap 13.6 g (0.092 moles) of CF$_3$CH=CFCl, formed by a mixture of cis/trans stereoisomers of the olefin in a ratio 40/60, are collected. The yield in product obtained by rearrangement, defined as the ratio between the obtained moles of CF$_3$—CH=CFCl and the starting moles of ClCF$_2$—CH=CF$_2$, is of 84.4%.
Characterization of 1-chloro-1,1,3,3-tetrafluoropropene
Boiling point =17° C. (referred to the stereoisomeric mixture)
+Isomer cis:
$^9$F-NMR in ppm referred to CFCl$_3$=0:
+59.2 (3F, CF$_3$—); −60.7 (1F, =CFCl).
$^1$H-NMR in ppm referred to TMS=0:
+5.3 (1H, —CH=).
+Isomer trans:
$^{19}$F-NMR in ppm referred to CFCl$_3$=0
+59.1 (3F, CF$_3$—); +62.0 (1F, =CFCl);
$^1$H-NMR in ppm referred to TMS=0:
+5.8 (1H, -CH=).
Mass spectrum (EI), main bands and attributions:
148 (M+); 129(M−F+); 113(M−Cl+, 100%); 69(CF$_3$+)
IR, main bands (cm$^{-1}$) (referred to the stereoisomeric mixture):
3128, 1748 (trans), 1691(cis), 1353, 1268, 1197, 1165, 1110, 1062, 859, 672.

Example 1d

Preparation of the 4-chloro-5-trifluoromethyl-2,2,4-trifluoro-1,3-dioxolane

In a 200 ml 5 necked reactor, equipped with a mechanical stirrer, thermocouple, bubbling inlet for introducing the reacting gaseous mixture and an inert gas, 51.3 g (0.346 moles) of CF$_3$—CH=CFCl are introduced. The reactor is then brought, by a cryostat, to the temperature of −70° C. At this point, under strong stirring, a mixture of CF$_2$(OF)$_2$ (BDM) (1 nl/h) and He (3 nl/h) for 3h 52' (equivalent to 0.173 moles of BDM) is added in a continuous way.

The reaction crude material is subjected to fractionated distillation in a plate column at atmospheric pressure. The substances reported hereunder together with the corresponding amounts are collected at the temperatures of 17°, 27° and 56° C., respectively, in the ±1° C. range:

17° C.: 13.1 g (0.088 moles) of unreacted $CF_3$—CH=CFCl.

27° C.: 21 g (0.113 moles) of $CF_3$—CHF—$CF_2Cl$

56° C.: 28.9 g (0.126 moles) of 4-chloro-5-trifluoromethyl-2,2,4-trifluoro-1,3-dioxolane.

The dioxolane yield expressed as ratio between the obtained dioxolane moles and the used BDM moles is of 72.8%.

Characterization of 4-chloro-5-trifluoromethyl-2,2,4-trifluoro-1,3-dioxolane

Boiling point: 56° C.
–Isomer anti:
$^{19}$F-NMR in ppm referred to $CFCl_3$=0:
F' and F'''=56.6 (2F,O—CF'F'''—O); –74.9 (3F,$CF_3$—); –68.3 (1F, —CFCl—)
$^{1}$H-NMR in ppm referred to TMS=0:
+5.12 (1H, -CH($CF_3$)).
–Isomer sin:
$^{19}$F-NMR in ppm referred to $CFCl_3$=0:
F''=–55.2; F'''=–56.8 (2F, O—CF'F'''—O), $J_{F'F'''}$=68 Hz; –75.8
(3F, $CF_3$-); –47.8 (1F, -CFCl-).
$^{1}$H-NMR in ppm referred to TMS=0:
+5.05 (1H, —CH($CF_3$)).

Mass spectrum (EI), mean bands and attributions:
195 (M-Cl+); 167 ($CF_3F_6HO+$, 100%); 161 (M—$CF_3$+); 148 ($C_3F_5HO+$)
101 ($C_2F_4H+$); 69 ($CF_3+$).

IR, main bands (cm$^{-1}$) (referred to the stereoisomeric mixture):
2998, 1383, 1307, 1279, 1194, 1116, 1078, 989, 921, 840, 707.

EXAMPLE 2

Dehydrohalogenation of 4-chloro-5-trifluoromethyl-2,2,4-trifluoro-1,3-dioxolane and obtainment of perfluoro-4-methyl-1,3-dioxole In a 50 ml three-necked glass flask, equipped with magnetic stirrer, thermometer, dropping funnel and cold trap (liq. $N_2$) directly connected to the flask by a retort, 9 g (0.039 moles) of dioxolane and 1.5 g (0.009 moles) of tetrabutylammonium hydroxide, are introduced. Under vigorous stirring and at the residual pressure of 400 mmHg, 12 ml of a 30% KOH aqueous solution (equivalent to 5.4 g or 0.097 moles of KOH) are dropped at room temperature. When the addition of the KOH solution is over, the residual pressure is lowered to 60 mmHg. In the cold trap 6.69 g of material, of which 4.5 g of perfluoro-4-methyl-1,3-dioxole and 2.19 g of unreacted dioxolane, are thus collected.

The yield in dehydrochlorination product calculated as ratio between the obtained dioxole moles and the starting dioxolane moles is equal to 61.3%. The reaction conversion is 84.3% and the selectivity of 72.7%.

Characterization of perfluoro-4-methyl-1,3-dioxole
Boiling point: 14–15° C.
$^{19}$F-NMR in ppm referred to $CFCl_3$=0:
–47.0 (2F, O—$CF_2$—O); –65.8(3F, $CF_3$—); –130.4 (1F, =CF—O).

Mass spectrum (EI), main bands and attributions:
194 (M+, 100%); 175 (M-F+); 147 ($C_3F_5O+$); 97 ($C_2F_3O+$); 69 ($CF_3+$).

IR, main bands (cm$^{-1}$):
1802, 1435, 1345, 1294, 1223, 1208, 1194, 1180, 1115, 1029, 992, 727, 491.

EXAMPLE 3

Copolymer 30/70 PMD/TFE

In a 50 ml steel reactor, equipped with magnetic stirrer and an inlet for the reactant feeding and discharge, 1 ml of $CCl_2FCF_2Cl$, 1 ml of perfluoropropionyl peroxide at 6% by weight in $CCl_2FCF_2Cl$, 15 mmoles of perfluoro-4-methyl-1,3-dioxole and 32 mmoles of tetrafluoroethylene are introduced.

The so charged reactor is brought to the temperature of –196° C. and evacuated; at the end of the degassing operations the reactor is brought to 30° C. and maintained at this temperature, under magnetic stirring, for 8 hours. The reactor is then cooled at the liquid nitrogen temperature, connected to a vacuum system maintained at the pressure of $10^{-3}$ mbar, and then allowed to reach the room temperature while fractionating the vapours by cooled traps, respectively, at –80° C., –120° C. and –196° C.

The trap content at –80° C., when the reaction was over, resulted to be the $CCl_2FCF_2Cl$ solvent only. In the trap at 120° C., 2.9 mmoles of $CCl_2FCF_2Cl$ and 8.2 mmoles of unreacted dioxole have been found. The trap at –196° C. contains 13.9 mmoles of unreacted $C_2F_4$. After solvent and unreacted monomer distillation, and subsequent stripping of the polymer under vacuum at the temperature of 150° C. for 3 hours, 2.21 g of polymer are isolated. The weight balance determined by g.l.c. of the unreacted monomers allows to calculate that the PMD % molar in the polymer is of 30%. The polymer Tg, determined by DSC, is 92° C. The TGA shows a weight loss of 10% at 495° C.

EXAMPLE 4

Copolymer 48/52 PMD/TFE

In a 50 ml steel reactor, equipped with magnetic stirrer and an inlet for the reactant feeding and discharge, 1 ml of perfluoropropionyl peroxide at 6% by weight of $CCl_2FCF_2Cl$, 6.5 mmoles of perfluoro-4-methyl-1,3-dioxole (PMD) and 10 mmoles of tetrafluoroethylene, are introduced.

The so charged reactor is brought to the temperature of –196° C. and evacuated; at the end of the degassing operations the reactor is brought to 30° C. and maintained at this temperature, under magnetic stirring, for 8 hours. The reactor is then cooled at the liquid nitrogen temperature, connected to a vacuum system maintained at the pressure of $10^3$ mbar, and then allowed to reach the room temperature. The vapours are fractionated by traps, cooled, respectively, at –80° C., –120° C. and –196° C.

At the end of the fractionation, the trap at –80° C. results to contain only $CCl_2FCF_2Cl$, the trap at –120° C 1.18 mmoles of $CCl_2FCF_2Cl$ and 6.1 mmoles of unreacted dioxole, the trap at –196° C. 9.57 mmoles of unreacted $C_2F_4$. After solvent and unreacted monomer distillation, and subsequent polymer stripping under vacuum at the temperature of 130° C. for 3 hours, 40 mg of polymer are isolated. The weight balance of the unreacted monomers, detrmined by g.l.c., allows to determine that the PDM % molar in the polymer is of 48 W. The TGA shows a weight loss of 10% at 327° C. The polymer Tg, determined by DSC, is 165° C.

EXAMPLE 5

Copolymer PMD/VDF (PDM 3%)

In a 50 ml steel reactor, equipped with magnetic stirrer and an inlet for the reactant feeding and discharge, 10 ml of $CCl_2FCF_2C_1$, 0.5 ml of perfluoropropionyl peroxide at 6% by weight in $CCl_2FCF_2Cl$, 9.2 mmoles of perfluoro-4-methyl-1,3-dioxole (PMD), are introduced.

The so charged reactor is brought to the temperature of –196° C. and evacuated; at the end of the degassing operations, the reactor is brought to 30° C. and VDF is pumped until the reactor internal pressure is of 18 atm. This temperature is maintained, under magnetic stirring, for 8 hours. The reactor is then cooled at the liquid nitrogen temperature, connected to a vacuum system maintained at the pressure of $10^3$ mbar, and then allowed to reach the room temperature, recovering the vapours in a cooled trap at −196° C.

After solvent and unreacted monomer distillation, and subsequent polymer stripping under vacuum at the temperature of 130° C. for 3 hours, 374 mg of polymer are isolated. The copolymer composition was determined by NMR since the compound is soluble in the aprotic polar solvents (DMF, acetone). It was thus calculated that the dioxole percentage is 3% (% moles). The polymer Tg, determined by DSC, is −38.6° C. The TGA shows a weight loss of 2% at 455° C. and of 10% at 478° C.

The AH and the second melting point, determined by DSC, are respectively of 11.59 cal/g and 157.97° C.

EXAMPLE 6
Copolymer 50/50 PMD/VDF

In a 50 ml steel reactor, equipped with magnetic stirrer and an inlet for the reactant feeding and discharge, 80 µl of perfluoropropionyl peroxide at 6% by weight in $CCl_2FCF_2Cl$ and 5 mmoles of perfluoro-4-methyl-1,3-dioxole (PMD) are introduced.

The charged reactor is brought to the temperature of −196° C. 10 mmoles of VDF are introduced by condensation and then the reactor is degassed; at the end of the degassing operations, the reactor is brought to 30° C. and maintained at this temperature, under magnetic stirring, for 4 hours. The reactor internal pressure changes from 4.5 atm to 3.3 atm. The reactor is then brought to the liquid nitrogen temperature and connected to a vacuum system maintained at the pressure of $10^{-3}$ mbar. The reactor is allowed to reach the room temperture, recovering the vapours in a cooled trap at −196° C.

After solvent and unreacted monomer distillation, and subsequent stripping of the polymer under vacuum at the temperature of 130° C. for 5 hours, 175 mg of polymer are isolated. The weight balance determined by g.l.c. of the unreacted monomers contained in the traps allows to calculate the PDM % molar in the polymer, which results to be 50%. The polymer Tg, determined by DSC, is 60.9° C. The TGA shows a weight loss of 10% at 301° C.

EXAMPLE 7 (COMPARATIVE)
Copolymer 32/68 TTD/TFE

In a 31 ml glass reactor, equipped with magnetic stirrer and a PTFE valve, 1 ml of $CFCl_2CF_2Cl$, 1 ml of perfluoropropionyl peroxide at 1.3% by weight in $CCl_2FCF_2Cl$, 5 mmoles of 2,2,4-trifluoro-5-trifluorometoxy-1,3-dioxole (TTD) and 10 mmoles of TFE are fed. The reactor is brought to −196° C., degas-ed, and then brought to the temperature of 40° C., at which it is maintained, under stirring, for 8 hours. After solvent and unreacted monomer distillation, and subsequent polymer stripping under vacuum at the temperature of 120° C. for 3 hours, 0.24 g of polymer are isolated. The weight balance determined by g.l.c. of the unreacted monomers contained in the traps allows to calculate that the TTD % molar in the polymer is of 32%. The polymer Tg, determined by DSC, is 82° C.

The TGA shows a weight loss of 2% at 381° and of 10% at 421° C.

EXAMPLE 8 (COMPARATIVE)

Copolymer 32/68 PD/TFE

In a 31 ml glass reactor, equipped with magnetic stirrer and a PTFE valve, 1 ml of $CFCl_2CF_2Cl$, 1 ml of perfluoropropionyl peroxide at 1.3% by weight of $CCl_2FCF_2Cl$, 4 mmoles of PD (2,2,4,5-tetrafluoro-1,3-dioxole) and 8 mmoles of TFE, are introduced. The reactor is brought to −196° C. and degassed. The reactor is then brought to the temperature of 40° C. and maintained at this temperature for 8 hours under stirring. After solvent and unreacted monomer distillation, and subsequent polymer stripping under vacuum at the temperature of 120° C. for 3 hours, 1.2 g of polymer are isolated. The weight balance determined by g.l.c. of the unreacted monomers contained in the traps, allows to calculate that the PD % molar in the polymer is of 32%. The polymer Tg, determined by DSC, is 90° C.

The AH and the second melting point, determined by DSC, are respectively: 3.8 cal/g and 314° C. The obtained polymer is therefore semicrystalline.

TABLE I

|  | Tg (° C.) |
| --- | --- |
| Copolymers of the invention |  |
| PMD/TFE 48/52* (ref. ex. 4) | 165 |
| PMD/TFE 30/70* (ref. ex. 3) | 92 |
| Copolymers of the prior art |  |
| PDD/TFE 50/50* (ref. U.S. Pat. No. 4,754,009) | 108 |
| PDD/TFE 30/70* (ref. U.S. Pat. No. 4,754,009) | 85 |
| PD/TFE 32/68* (ref. ex. 8) | 90 |
| TTD/TFE 32/68* (ref. ex. 7) | 82 |

*Molar ratio

What is claimed is:
1. Copolymers obtained with compounds of formula (II)

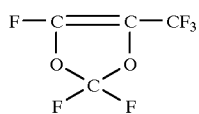

(II)

and comonomers containing olefinic unsaturations, containing from 0.1 to 50% by moles of the following unit:

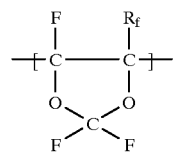

(III)

wherein $R_f$ is $CF_3$, and wherein the copolymers have a higher thermal stability than copolymers, obtained without compounds of formula (II), which contain the same molar percentage of fluorinated dioxoles.

2. The copolymers according to claim 1 wherein the comonomer is selected from the group consisting of tetrafluoroethylene, vinyilidene fluoride, vinyl fluoride, trifluoroethylene, perfluoropropene, perfluoromethylvinyleher, perfluoroethylvinylether, perfluorodioxole, perfluoro (2,2-dimethyl)-1,3-dioxole, perfluoro-4-methoxy-1,3-dioxole, $CF_2$=CF—O—$CF_2$—$CF_2$—$SO_2F$, chlorotrifluoroethylene, vinyl chloride, methyl acrylate, methyl methacrylate, or ethylene.

3. The copolymers according to claim 2 wherein the comonomer is tetrafluoroethylene.

4. A process for preparing copolymers according to claim 1 comprising copolymerizing the comonomers in the presence of polymerization initiators in aqueous or organic medium.

* * * * *